United States Patent
Gregoire et al.

(10) Patent No.: US 9,041,408 B2
(45) Date of Patent: May 26, 2015

(54) REMOVABLE SURFACE-WAVE NETWORKS FOR IN-SITU MATERIAL HEALTH MONITORING

(71) Applicant: HRL LABORATORIES, LLC, Malibu, CA (US)

(72) Inventors: Daniel J. Gregoire, Thousand Oaks, CA (US); Joseph S. Colburn, Malibu, CA (US)

(73) Assignee: HRL Laboratories, LLC, Malibu, CA (US)

( * ) Notice: Subject to any disclaimer, the term of this patent is extended or adjusted under 35 U.S.C. 154(b) by 240 days.

(21) Appl. No.: 13/742,831

(22) Filed: Jan. 16, 2013

(65) Prior Publication Data
US 2014/0197848 A1    Jul. 17, 2014

(51) Int. Cl.
| | |
|---|---|
| G01R 31/08 | (2006.01) |
| G01N 3/00 | (2006.01) |
| G01N 22/02 | (2006.01) |
| H01Q 13/20 | (2006.01) |
| G01M 99/00 | (2011.01) |

(52) U.S. Cl.
CPC .............. *G01N 3/00* (2013.01); *G01N 22/02* (2013.01); *H01Q 13/20* (2013.01); *G01M 99/00* (2013.01)

(58) Field of Classification Search
CPC ........................................ G01R 29/08
USPC .......................................... 324/637
See application file for complete search history.

(56) References Cited

U.S. PATENT DOCUMENTS

| | | | |
|---|---|---|---|
| 3,634,753 A | 1/1972 | Unterberger | 324/337 |
| 3,665,466 A | 5/1972 | Hibbard | 342/59 |
| 3,891,979 A | 6/1975 | Braun et al. | 340/581 |
| 3,946,338 A * | 3/1976 | Schmidt | 333/153 |
| 4,094,304 A * | 6/1978 | Wright, Jr. | 600/552 |
| 4,274,288 A * | 6/1981 | Tittmann et al. | 73/602 |
| 4,882,714 A * | 11/1989 | Tanigawa | 367/103 |
| 4,891,796 A * | 1/1990 | Sekine | 367/96 |
| 4,892,906 A | 1/1990 | Pham et al. | |
| 5,340,715 A * | 8/1994 | Slovacek et al. | 435/6.11 |
| 5,525,466 A * | 6/1996 | Slovacek et al. | 435/6.11 |
| 5,650,461 A | 7/1997 | Wasserman et al. | |
| 5,695,155 A * | 12/1997 | Macdonald et al. | 244/134 F |
| 5,818,341 A * | 10/1998 | Saurer et al. | 340/602 |
| 6,186,006 B1 * | 2/2001 | Schmitz et al. | 73/598 |

(Continued)

OTHER PUBLICATIONS

Daniels, "On the Ionization of Air for Removal of Noxious Effluvia" (Air Ionization of Indoor Environments for Control of Volatile and Particulate Contaminants with Nonthermal Plasmas Generated by Dielectric-Barrier Discharge), IEEE Transactions on Plasma Science, vol. 30, No. 4, Aug. 2002, pp. 1471-1481.

(Continued)

*Primary Examiner* — Benjamin M Baldridge
(74) *Attorney, Agent, or Firm* — Ladas & Parry (57) ABSTRACT

A system for measuring properties of a surface under test with surface waves includes a surface wave network including a dielectric substrate, a reactive grid of a plurality of metallic patches on a first surface of the dielectric substrate, a plurality of electronic nodes on the first surface of the dielectric substrate, and a ground plane on a second surface of the dielectric substrate permeable to RF fields of the surface waves, and a controller configured for causing a respective one of the electronic nodes to transmit at least one surface wave and configured for collecting data for signals received by at least one other of the plurality of electronic nodes.

31 Claims, 8 Drawing Sheets

(56) References Cited

U.S. PATENT DOCUMENTS

| | | | |
|---|---|---|---|
| 6,245,126 B1 | 6/2001 | Feldman et al. | 95/59 |
| 6,255,831 B1* | 7/2001 | Mayer | 324/636 |
| 6,320,401 B1* | 11/2001 | Sugimoto et al. | 324/754.31 |
| 6,531,537 B2 | 3/2003 | Friel et al. | |
| 6,556,146 B1* | 4/2003 | Ruile et al. | 340/870.3 |
| 6,943,887 B2* | 9/2005 | Quinn et al. | 356/445 |
| 7,525,398 B2* | 4/2009 | Nishimura et al. | 333/189 |
| 7,719,694 B1* | 5/2010 | Gregoire | 356/601 |
| 7,931,858 B1* | 4/2011 | Gross et al. | 422/22 |
| 8,009,276 B1* | 8/2011 | Kirby et al. | 356/32 |
| 8,017,217 B1* | 9/2011 | Gregoire et al. | 428/137 |
| 2003/0165636 A1 | 9/2003 | Koulik et al. | 427/569 |
| 2004/0042077 A1 | 3/2004 | Birge et al. | |
| 2004/0100278 A1* | 5/2004 | Haycock | 324/637 |
| 2004/0164682 A1 | 8/2004 | Hopwood et al. | |
| 2004/0175407 A1 | 9/2004 | McDaniel | |
| 2004/0224145 A1 | 11/2004 | Weir et al. | |
| 2004/0256056 A1 | 12/2004 | Hall et al. | |
| 2004/0262521 A1* | 12/2004 | Devitt et al. | 250/341.1 |
| 2005/0057263 A1* | 3/2005 | Moshe et al. | 324/637 |
| 2005/0058689 A1 | 3/2005 | McDaniel | |
| 2005/0126441 A1 | 6/2005 | Skelhorn | |
| 2006/0141003 A1 | 6/2006 | McDaniel | |
| 2006/0225164 A1* | 10/2006 | Williams et al. | 977/852 |
| 2008/0129316 A1* | 6/2008 | Zoughi et al. | 324/637 |
| 2008/0319375 A1 | 12/2008 | Hardy | 604/22 |
| 2009/0135183 A1* | 5/2009 | Sato et al. | 345/426 |
| 2009/0309011 A1* | 12/2009 | Ramahi et al. | 250/227.11 |
| 2010/0171518 A1* | 7/2010 | Bateman et al. | 324/724 |
| 2013/0154668 A1* | 6/2013 | Leflour | 324/637 |
| 2014/0002107 A9* | 1/2014 | Leflour | 324/637 |
| 2014/0241112 A1* | 8/2014 | Kano | 367/7 |

OTHER PUBLICATIONS

Deng, et al., "Physical Mechanisms of Inactivation of *Bacillus subtilis* Spores Using Cold Atmospheric Plasmas", IEEE Transactions on Plasma Science, vol. 34, No. 4, Aug. 2006, pp. 1310-1316.

Hermann, et al., "Chemical Warfare Agent Decontamination Studies in the Plasma Decon Chamber", IEEE Transactions on Plasma Science, vol. 30, No. 4, Aug. 2002, pp. 1460-1470.

Laroussi, "Nonthermal Decontamination of Biological Media by Atmospheric-Pressure Plasmas: Review Analysis and Prospects", IEEE Transactions Plasma Science, vol. 30, No. 4, Aug. 2002, pp. 1409-1415.

Montie, et al. "An Overview of Research Using the One Atmosphere Uniform Glow Discharge Plasma (OAUGDP) for Sterilization of Surfaces and Materials", IEEE Transactions on Plasma Science, vol. 28, No. 1, Feb. 2000, pp. 41-50.

\* cited by examiner

```
┌─────────────────────────────────────────────────────┐
│  REMOVABLY LOCATING A SURFACE WAVE NETWORK ON THE   │
│  SURFACE UNDER TEST                           100   │
└─────────────────────────────────────────────────────┘
                            │
┌─────────────────────────────────────────────────────┐
│  WHEREIN THE SURFACE WAVE NETWORK COMPRISES:        │
│      A DIELECTRIC SUBSTRATE;                  102   │
│      A REACTIVE GRID COMPRISING A PLURALITY OF      │
│  METALLIC PATCHES ON A FIRST SURFACE OF THE         │
│  DIELECTRIC SUBSTRATE;                              │
│        A PLURALITY OF ELECTRONIC NODES ON THE       │
│  FIRST SURFACE OF THE DIELECTRIC SUBSTRATE; AND     │
│        A GROUND PLANE ON A SECOND SURFACE OF THE    │
│  DIELECTRIC SUBSTRATE OPPOSITE THE FIRST            │
│  SURFACE OF THE DIELECTRIC SUBSTRATE, THE           │
│  GROUND PLANE PERMEABLE TO RF FIELDS OF THE         │
│  SURFACE WAVES                                      │
└─────────────────────────────────────────────────────┘
```

FIG. 6A

```
┌─────────────────────────────────────────────────┐
│ OPERATING A CONTROLLER CONFIGURED FOR CAUSING A │
│ RESPECTIVE ONE OF THE ELECTRONIC NODES TO TRANSMIT│
│ AT LEAST ONE SURFACE WAVE AND CONFIGURED FOR    │
│ COLLECTING DATA FOR SIGNALS RECEIVED BY AT LEAST│
│ ONE OTHER OF THE PLURALITY OF ELECTRONIC NODES  │ 104
└─────────────────────────────────────────────────┘
                        │
┌─────────────────────────────────────────────────┐
│ PROCESSING THE COLLECTED DATA TO DETERMINE THE  │ 106
│ SURFACE CHARACTERISTIC OF THE SURFACE UNDER TEST│
└─────────────────────────────────────────────────┘
                        │
┌─────────────────────────────────────────────────┐
│ WHEREIN PROCESSING THE COLLECTED DATA FURTHER   │ 108
│ COMPRISES COMPARING THE COLLECTED DATA TO BASELINE│
│ COLLECTED DATA FROM A DAMAGE-FREE SURFACE       │
└─────────────────────────────────────────────────┘
                        │
┌─────────────────────────────────────────────────┐
│ WHEREIN COMPARING THE COLLECTED DATA TO BASELINE│
│ COLLECTED DATA FROM A DAMAGE-FREE SURFACE FURTHER│
│ COMPRISES CREATING AN IMAGE OF THE DAMAGE TO THE│ 110
│ SURFACE                                         │
└─────────────────────────────────────────────────┘
```

FIG. 6B

REMOVABLE SURFACE-WAVE NETWORKS FOR IN-SITU MATERIAL HEALTH MONITORING

CROSS REFERENCE TO RELATED APPLICATIONS

This application is related to U.S. Pat. No. 7,719,694 issued May 18, 2010, to U.S. Pat. No. 8,009,276 issued Aug. 30, 2011, and to U.S. Pat. No. 7,931,858 issued Apr. 26, 2011, which are incorporated herein by reference, as though laid out in full.

TECHNICAL FIELD

This disclosure relates to measuring radio frequency (RF) and mechanical properties of a surface under test (SUT).

BACKGROUND

There are two prior art commonly used ways to measure the properties of a surface under test. The first method requires visual inspection in which a technician closely examines the surface under test (SUT) for damage and defects, and compares suspected damage to previously recorded inspections. The visual inspection is performed using visible light or can be performed with IR or microwave imagers. The second method uses handheld probes that the technician meticulously scans across the SUT. The handheld probe typically evaluates a small area at a time.

Both of these methods are very time consuming, and difficult to perform on SUTs that lie on concave surfaces with small openings. Visual inspection methods are subjective and open to interpretation.

Also in the prior art are health monitoring systems that use acoustic surface waves (ASW) to determine structural mechanical properties. While the ASW methods can be used to monitor mechanical health, the ASW methods are not suited for detecting changes in static/lightning charge dissipation and RF properties in the SUT, especially at electromagnetic frequencies greater than 1.0 GHz. ASW methods monitor only the mechanical properties of the SUT.

In U.S. Pat. No. 7,719,694, issued May 18, 2010, another method is disclosed of using surface wave imaging to detect damage on a surface. A surface wave network (SWN) is described that is integrated within the SUT to allow for rapid real-time in-situ diagnostics. The surface-wave medium described in U.S. Pat. No. 7,719,694 is integral with the SUT and is not removable.

Another method used for evaluating the health of RF surfaces is inverse synthetic aperture radar (ISAR) imaging. ISAR imaging requires the use of expensive equipment and time-consuming processing. It also requires the imaging sensors to be sufficiently removed from the SUT, and ISAR imaging is not capable of measuring SUT properties in concave, re-entrant spaces.

What is needed is a low cost and rapid method of monitoring the material health of a surface under test (SUT) that can be used to monitor the mechanical and RF properties of the SUT, and which is not integral to the SUT. The embodiments of the present disclosure answer these and other needs.

SUMMARY

In a first embodiment disclosed herein, a system for measuring properties of a surface under test with surface waves, the system comprises a surface wave network comprising a dielectric substrate, a reactive grid comprising a plurality of metallic patches on a first surface of the dielectric substrate, a plurality of electronic nodes on the first surface of the dielectric substrate, and a ground plane on a second surface of the dielectric substrate opposite the first surface of the dielectric substrate, the ground plane permeable to radio frequency fields of the surface waves, and a controller configured for causing a respective one of the electronic nodes to transmit at least one surface wave and configured for collecting data for signals received by at least one other of the plurality of electronic nodes.

In another embodiment disclosed herein, a method of of determining a surface characteristic of a surface under test comprises removably locating a surface wave network on the surface under test, wherein the surface wave network comprises a dielectric substrate, a reactive grid comprising a plurality of metallic patches on a first surface of the dielectric substrate, a plurality of electronic nodes on the first surface of the dielectric substrate, and a ground plane on a second surface of the dielectric substrate opposite the first surface of the dielectric substrate, the ground plane permeable to radio frequency fields of the surface waves, operating a controller configured for causing a respective one of the electronic nodes to transmit at least one surface wave and configured for collecting data for signals received by at least one other of the plurality of electronic nodes, and processing the collected data to determine the surface characteristic of the surface under test.

In yet another embodiment disclosed herein, an apparatus for measuring properties of a surface under test with surface waves comprises a surface wave network comprising a dielectric substrate, a reactive grid comprising a plurality of metallic patches on a first surface of the dielectric substrate, a plurality of electronic nodes on the first surface of the dielectric substrate, and a ground plane on a second surface of the dielectric substrate opposite the first surface of the dielectric substrate, the ground plane permeable to radio frequency fields of the surface waves.

These and other features and advantages will become further apparent from the detailed description and accompanying figures that follow. In the figures and description, numerals indicate the various features, like numerals referring to like features throughout both the drawings and the description.

DETAILED DESCRIPTION

In the following description, numerous specific details are set forth to clearly describe various specific embodiments disclosed herein. One skilled in the art, however, will understand that the presently claimed invention may be practiced without all of the specific details discussed below. In other instances, well known features have not been described so as not to obscure the invention.

Figure 1A:
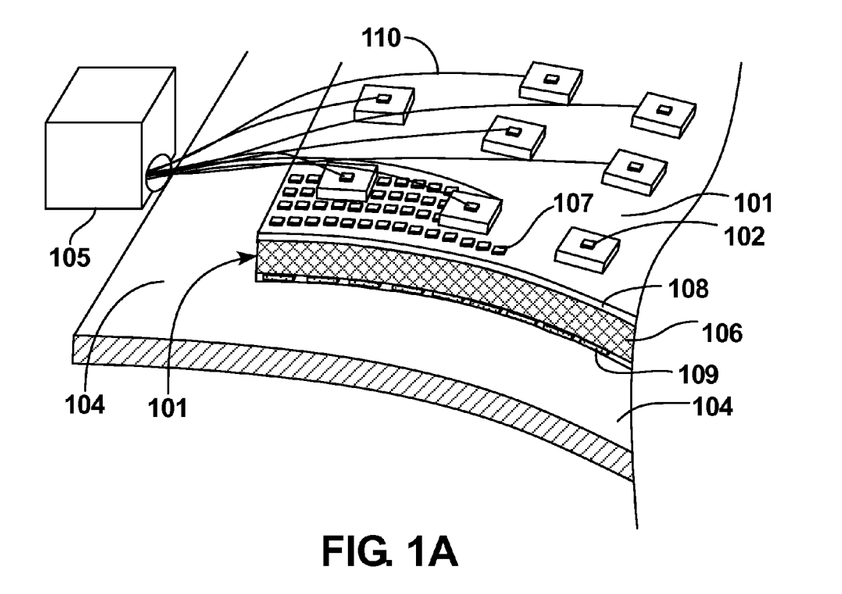
FIGS. 1A-1C show a surface-wave network (SWN) in accordance with the present disclosure.
Figure 1B:
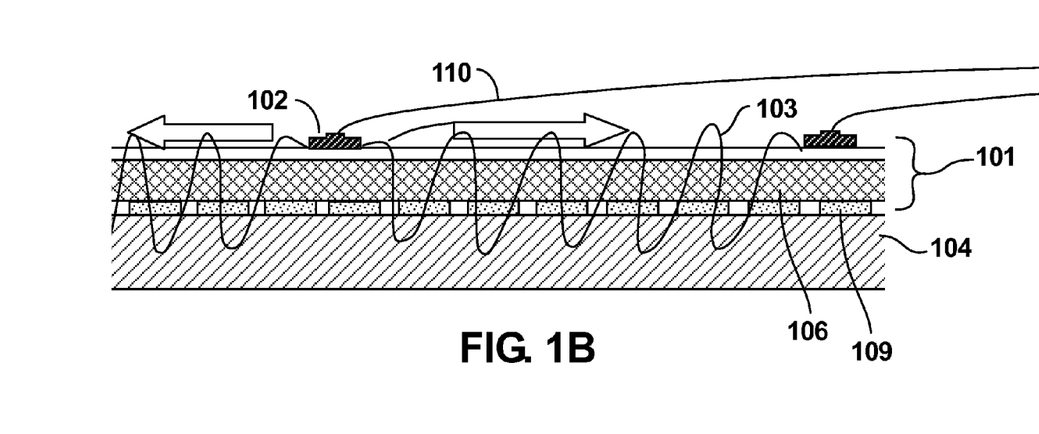
Figure 1C:
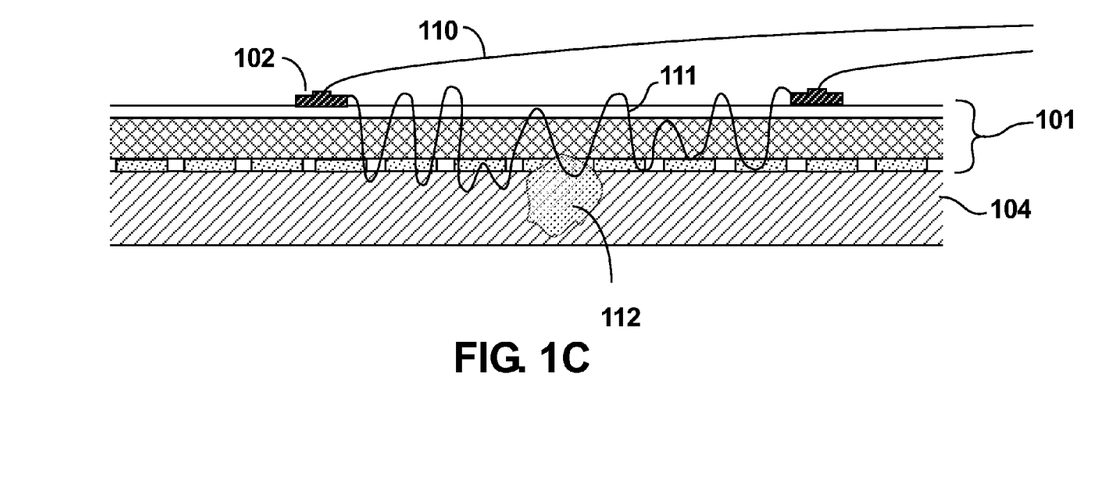

Referring to FIGS. 1A, 1B and 1C, a surface-wave network (SWN) 101 is shown that consists of laminated structured metamaterial that supports electromagnetic surface-wave propagation 103, as shown in FIG. 1B. The SWN 101 has embedded on its surface numerous electronic nodes 102. Each node communicates with neighboring nodes via electromagnetic surface waves 103 bound to the surface of the SWN. Each node 102 is controlled by and exchanges data with a central control hub 105. The communication between a node 102 and the control hub 105 can be via wires 110 or be wireless using any wireless communication method, such as Bluetooth.

To measure the properties of a SUT 104, the SWN 101 is placed onto and in contact with the SUT 104. The SWN 101 is separate from the SUT 104 and can be removed when the evaluation is complete. SUT 104 defects or damage are detected by measuring the propagation of surface waves between the nodes 102 in the SWN 101. The SUT 104 may be a substrate, an aircraft surface, or any other surface. One particular application is for detecting defects in composite surfaces and surfaces with non-metal treatments designed to control static charge build up, lighting protection and/or electromagnetic wave propagation.

The surface wave 103 fields extend below the SWN substrate into the SUT 104. Therefore the SUT 104 properties affect the surface wave propagation. Any changes in the SUT 104 from its nominal design are evident in the surface wave propagation, which is affected by the SUT's RF character. A defect in the SUT 104, as shown by defect 112 in FIG. 1C, may be located and characterized by processing the inter-node surface-wave propagation 111, shown in FIG. 1C, for changes due to the defect. When the surface wave encounters a defect in the SUT 104, its propagation is modified by reflection, refraction or attenuation from the defect. The phase and amplitude of the modified surface wave 111 is measured at the neighboring nodes.

The laminated RF metamaterial 101 used for the SWN 101 is also known as a surface-wave medium (SWM). The laminated RF metamaterial 101 may be formed using methods well known in the state of the art. In one method, a reactive grid of metallic patches 107 is printed on a dielectric substrate 106 with a permeable metallic ground plane 109. The patches 107 may be printed directly on the dielectric substrate 106 or they may be printed on a thin dielectric sheet 108 that is then laminated to the substrate 106.

The ground plane 109 is permeable to the RF fields of the surface waves 103. As shown in FIG. 1B, the surface-wave (SW) fields extend below the SWM ground plane 109 into the SUT 104. The extension of the SW fields into the SUT has the effect that the SW propagation is affected by the SUT properties.

Figure 2:
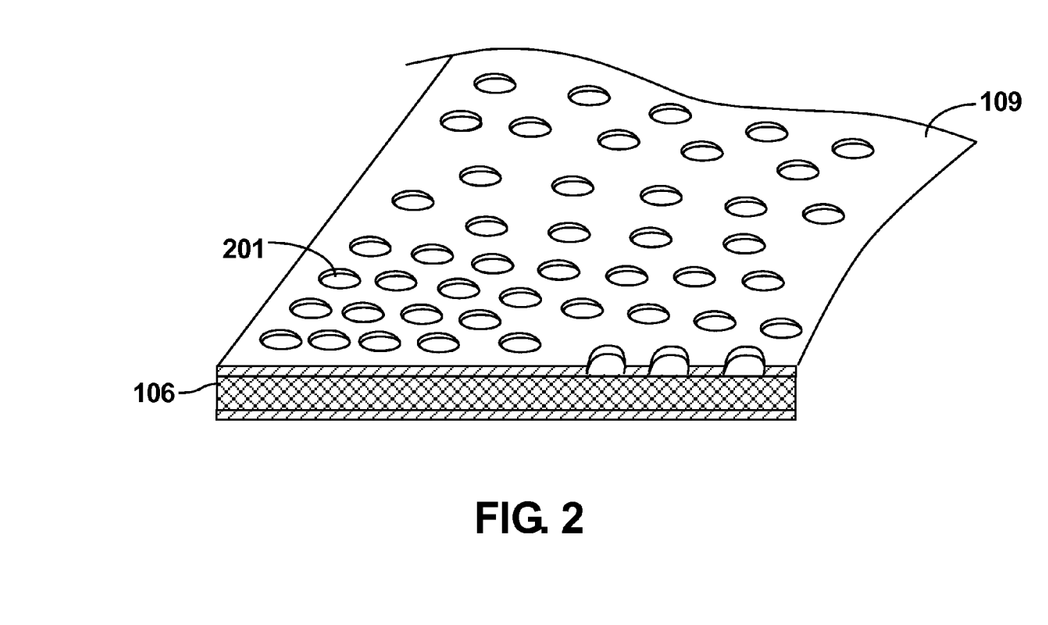
FIG. 2 shows a surface-wave medium (SWM) in accordance with the present disclosure.

The SWM ground plane 109 is made permeable to the SW fields by perforating it with an array of holes 201, as shown in FIG. 2. The size and spacing of the holes determines the penetration of the surface-wave (SW) fields through the ground plane 109. The larger the holes 201 are, the more the SW fields penetrate through the ground plane 209 into the SUT 104. The optimal hole size and spacing can be calculated analytically or with simulations using standard electromagnetic methods well known in the state of the art, and may be specific to the SW frequency and the SUT properties.

Figure 3A:
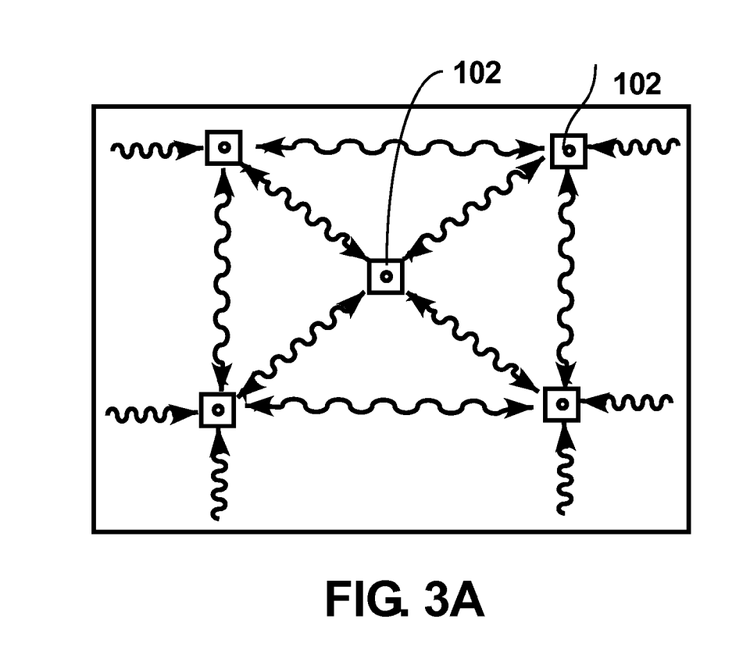
FIGS. 3A and 3B illustrate the method of detecting defects or damage in the SUT in accordance with the present disclosure.
Figure 3B:
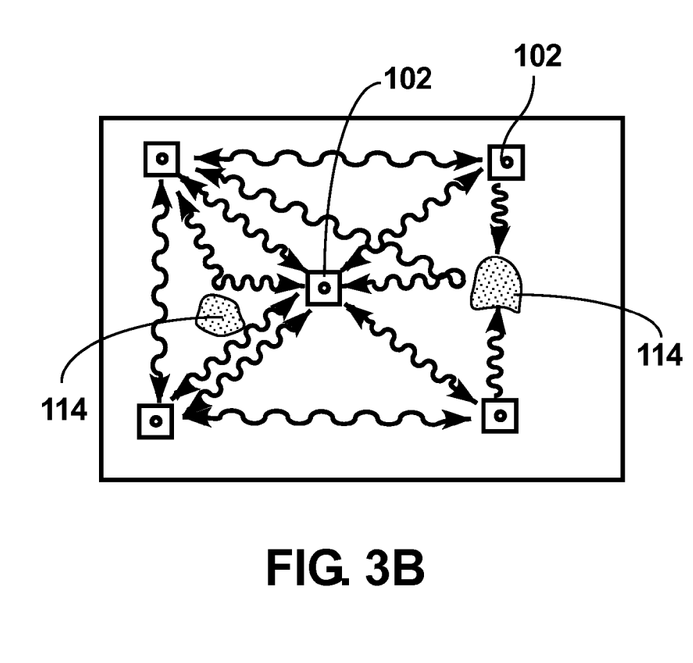

The method of detecting defects or damage in the SUT is illustrated in FIGS. 3A and 3B. The baseline properties of the SUT 104 may be first measured before the SUT 104 is exposed to harsh environments that can cause damage. FIG. 3A illustrates a baseline measurement done before the SUT has incurred any damage. In FIG. 3A the surface waves are depicted as propagating along simple paths between nodes 102 on the SWN 101. In reality, the surface-wave paths are much more complicated than what is depicted. The point is that a baseline of the SW fields propagating between nodes may be documented and stored in a data base for future comparison. Later, after the SUT has been exposed to outside influences that could have caused damage, the SW fields are measured again and compared to the baseline measurements. FIG. 3B depicts the SW propagation paths as modified by damage 114 in the SUT, showing reflection, refraction and attenuation by the defects.

In practice, the SW propagation signature may be determined by systematically measuring the phase and amplitude variation between each pair of nodes 102 in the SWN 101. If there are N nodes in the network, $N*(N-1)/2$ measurements are made. It may be possible to reduce the number of measurements if only the data from the nodes nearest to a defect are required to locate and characterize the defect. For example, if each node only has to be measured for the SW propagation to its M nearest neighbors, then only $M*N/2$ measurements need to be made.

The control hub 105 presides over the measurements between the nodes 102. The control hub 105 incorporates software and hardware capable of controlling SW transmissions from each node 102 and measuring and recording the received SW phase and magnitude at the other nodes 102. The control hub 105 commands each node 102 in turn to transmit a SW signal across the SWM 101. When one node 102 is transmitting, the other nodes 102 are in receive-only mode. The control hub 102 then interrogates each receiving node 102 for the phase and amplitude of the signal it received. All the collected data may be stored in a data base that is processed to create an image of the SUT 104 properties. The SW signal transmitted may be over a wide range of frequencies.

The image formed may then be compared to an image based on the baseline measurements. Then the control hub 105 may create and display a visual picture depicting any changes in the SUT properties from the baseline, and alert a technician operating the system to inspect the suspected area on the SUT 104 to confirm and possibly correct the damage.

There are many options for dividing the software and hardware requirements between the control hub 105 and the nodes 102. In one instance, the control hub 105 can contain all the RF, control and processing capability and the node 102 is simply a passive SW launcher. In this case, each node 102 may be connected to the control hub 105 with an RF coaxial cable. The control hub 105 may contain an RF switching network that systematically controls the launching of an RF signal from one node 102 to another node 102 and measures the phase and amplitude characteristic of the received signal. This is repeated in turn for each possible pair of nodes 102. The advantage of this embodiment is that all of the RF and processing complexity is built into the control hub 105, and the SWN 101 is a passive structure that doesn't have complex RF or digital components that are susceptible to damage and failure themselves.

In another embodiment, the node 102 contains the RF hardware that launches the surface wave, and other RF components that measures the phase and magnitude of received SW signals. Such phase and magnitude discriminators are readily available in low-cost IC components that interpret the relative signals as voltage outputs that may be digitized by the control hub 105. Alternately, the node 102 can also contain an analog-to-digital converter that converts the voltage signals to digital data. The digital data may then be read by or sent to the control hub 105 to be processed. The advantage of this embodiment is that it is potentially faster.

The SWN may be used to measure the properties of flat or singly-curved SUTs. Singly curved means the SUT can be formed by bending or folding a flat sheet. For example, a cylinder is singly curved. When very large flat or singly-curved SUTs are measured, an SWN 101 that is substantially smaller in size or area than the SUT 104 can be used by moving the SWN from place to place on the SUT. Construction of the full SUT image is created by the control hub 105 processing algorithm. The SWN 101 can be made flexible so that it is versatile enough to fit onto SUT's of various shapes by fabricating it with a substrate 106 that is a flexible dielectric.

The substrate 106 may also be both flexible in the sense that it bends and also stretchable, which allows the SWN 101 to be used to measure the properties of SUTs of various shapes including complex curvatures. The SWN can be flexed and stretched to fit onto the SUT. When the SWN 101 is stretchable, it is necessary to map out the positions of the nodes 102 with respect to the SUT 104 in order to correlate the measured data to positions on the SUT surface.

Figure 4:
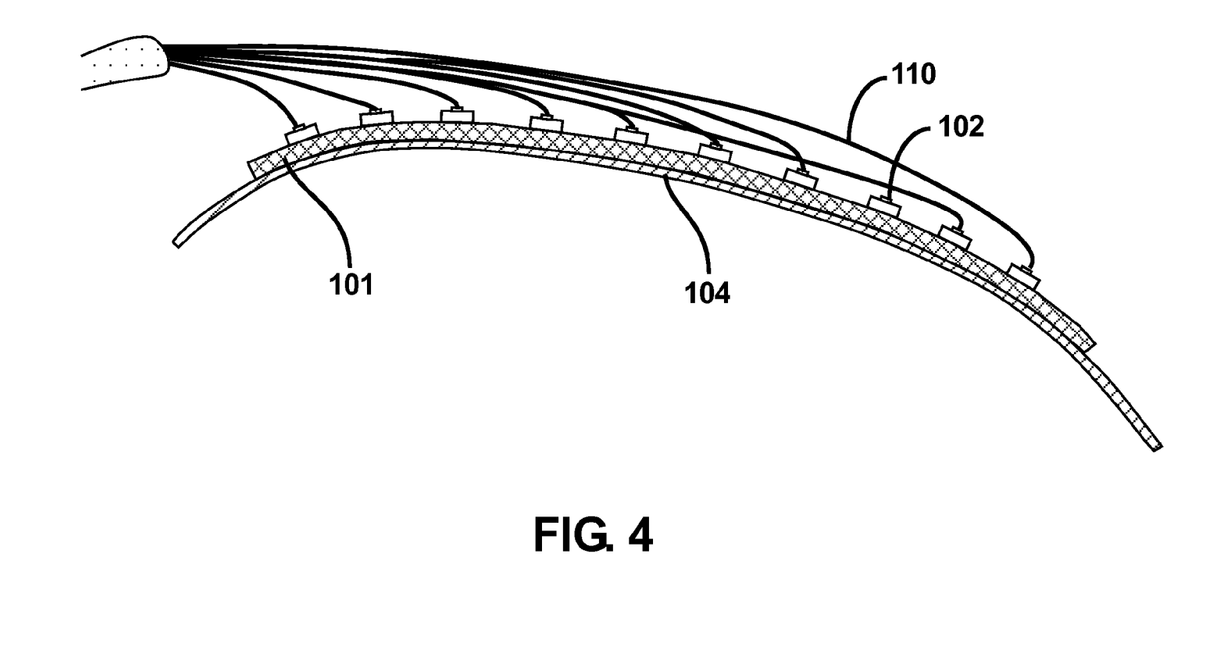
FIG. 4 shows a SWN overlaying an SUT with a complex curvature in accordance with the present disclosure.

The SWN may also be custom designed for a particular contoured SUT shape. This is particularly useful for an item that has many identical copies in use, and each one of them needs to be tested periodically. For example, the surface of a complex-shaped component on an aircraft. The health of contoured SUTs can be monitored with the custom SWN by designing the SWN with a curvature that matches the SUT's curvature, so that it conforms to the SUT curvature. The SWN may be indexed so that the node 102 positions with respect to reference positions on the SUT 104 are known. FIG. 4 illustrates a custom SWN 101 that lays on an SUT 104 with a complex curvature.

Figure 5A:
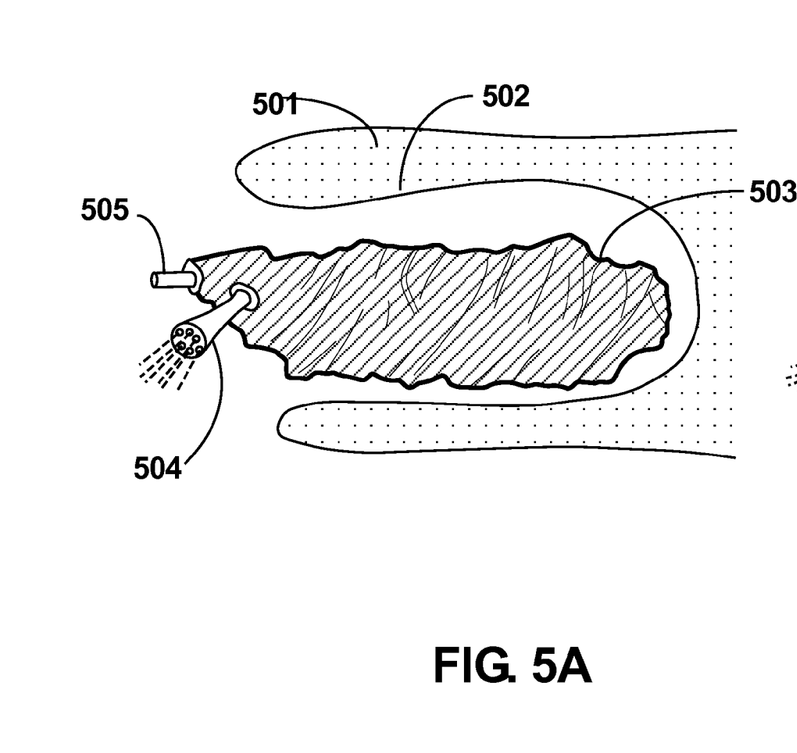
FIGS. 5A and 5B show a SWN for measuring the properties of an SUT with an inside reentrant cavity in accordance with the present disclosure.
Figure 5B:
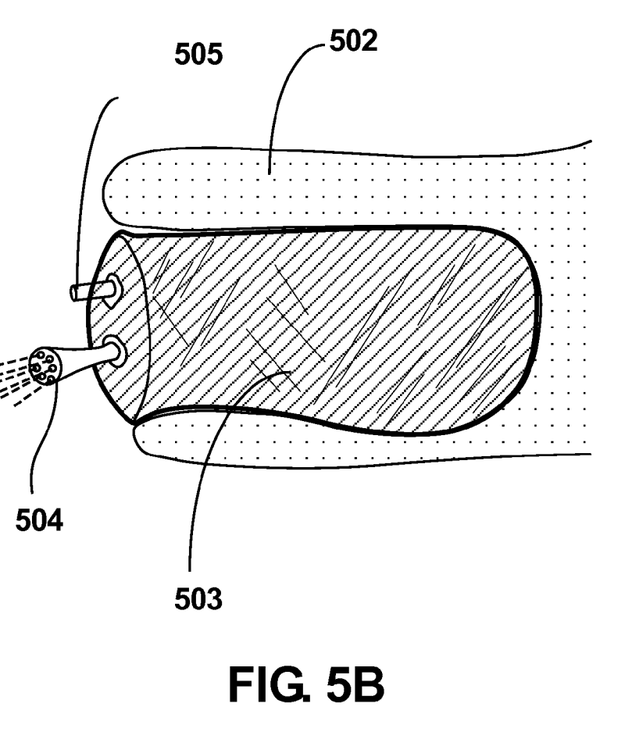

An SUT 502 that is inside of a concave cavity with a re-entrant shape 501 poses a special problem for periodic evaluation, especially if the opening of the cavity is too small for access for visual inspection or with remote robotic sensing devices. The SWN 503 may be used for evaluating such an SUT, and the measurements may be rapid and provide an accurate evaluation of the SUT.

Referring to FIGS. 5A and 5B, the SWN 503 for SUTs 502 on the inside of reentrant cavities may be implemented on a bladder-type structure that expands to mate with the SUT 502. The SWN 503 may be custom fit to exactly match the cavity interior when inflated. After evaluation, the SWN 503 may be removed from the substrate and stored for later use. The nodes 102 may be distributed on the inside of the bladder SWN 503, and the permeable ground plane 109 may be located on the outside of the bladder SWN 503. The control lines from the control hub 105 to the nodes 102 may be configured to pass through a pneumatic cable feedthrough 504, and the bladder SWN 503 may be inflated pneumatically through an air inlet 505.

In summary, a method of monitoring the material health of a surface under test (SUT) using a removable surface-wave network (SWN) has been described. The surface-wave network includes a laminated structured metamaterial substrate with a distribution of electronic nodes embedded on its surface. The metamaterial substrate supports electromagnetic surface-wave propagation. The bottom of the SWN substrate is placed in contact with the SUT, and it is electromagnetically permeable so that the SUT affects the propagation characteristics of surface waves in the SWN. The properties of the SUT are determined by measuring the surface-wave propagation among the nodes. If a defect caused by impact, cracking or material degradation occurs, it affects the propagation of surface waves. The quality, size and location of the defect can then be determined by processing the SW propagation data.

Figure 6A:
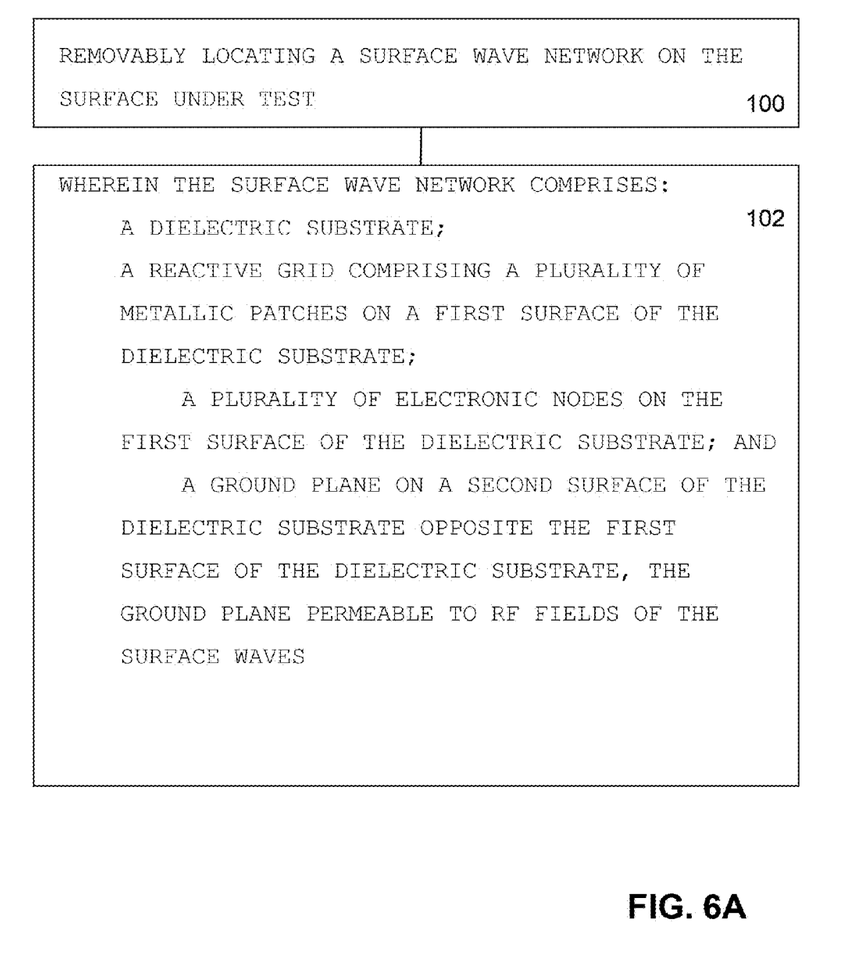
FIGS. 6A and 6B show a flow diagram of a method of determining a surface characteristic of a surface under test in accordance with the present disclosure.
Figure 6B:
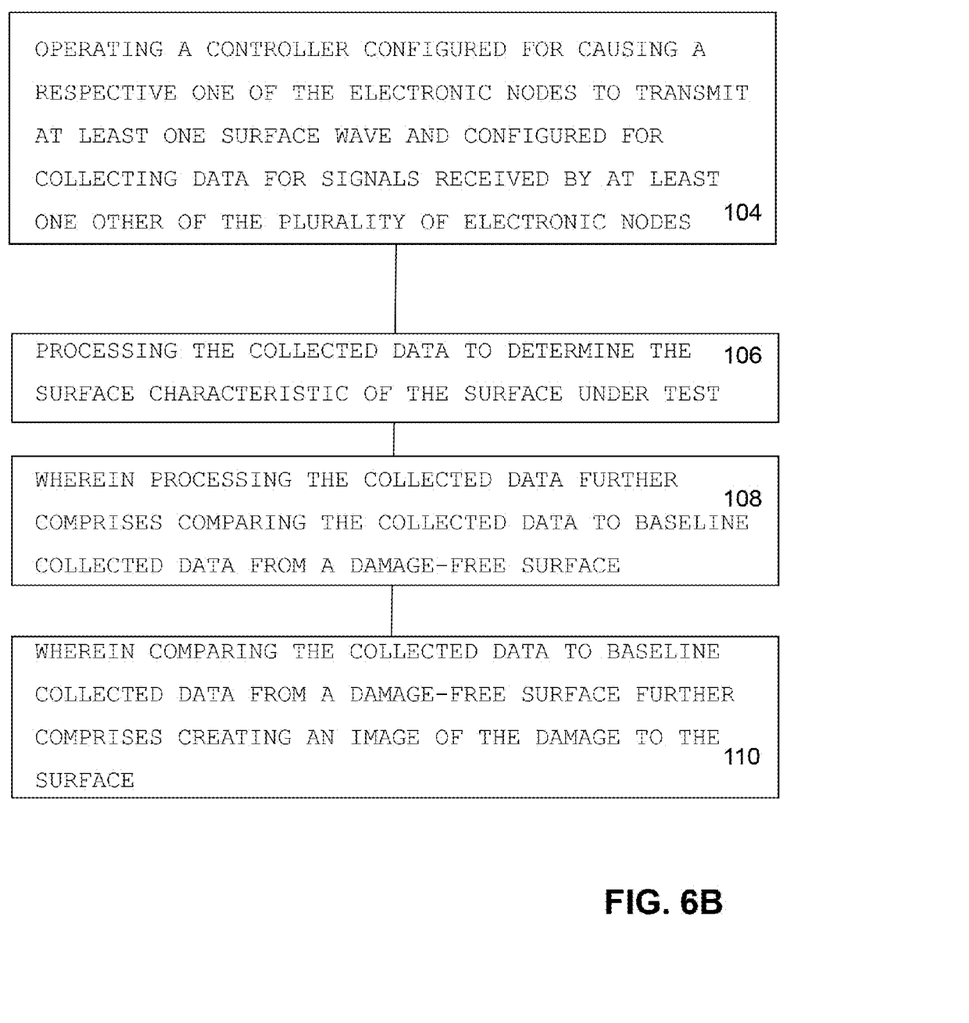

FIGS. 6A and 6B show a flow diagram of a method of determining a surface characteristic of a surface under test. In step 100 a surface wave network is removably located on the surface under test. In step 102 the surface wave network is shown to include a dielectric substrate, a reactive grid having a plurality of metallic patches on a first surface of the dielectric substrate, a plurality of electronic nodes on the first surface of the dielectric substrate, and a ground plane on a second surface of the dielectric substrate opposite the first surface of the dielectric substrate, the ground plane permeable to RF fields of the surface waves.

In step 104 a controller is operated, the controller configured for causing a respective one of the electronic nodes to transmit at least one surface wave and configured for collecting data for signals received by at least one other of the plurality of electronic nodes. Then in step 106 the collected data is processed to determine the surface characteristic of the surface under test.

In step 108, processing the collected data includes comparing the collected data to baseline collected data from a damage-free surface.

In step 110, comparing the collected data to baseline collected data from a damage-free surface includes creating an image of the damage to the surface.

Having now described the invention in accordance with the requirements of the patent statutes, those skilled in this art will understand how to make changes and modifications to the present invention to meet their specific requirements or conditions. Such changes and modifications may be made without departing from the scope and spirit of the invention as disclosed herein.

The foregoing Detailed Description of exemplary and preferred embodiments is presented for purposes of illustration and disclosure in accordance with the requirements of the law. It is not intended to be exhaustive nor to limit the invention to the precise form(s) described, but only to enable others skilled in the art to understand how the invention may be suited for a particular use or implementation. The possibility of modifications and variations will be apparent to practitioners skilled in the art. No limitation is intended by the description of exemplary embodiments which may have included tolerances, feature dimensions, specific operating conditions, engineering specifications, or the like, and which may vary between implementations or with changes to the state of the art, and no limitation should be implied therefrom. Applicant has made this disclosure with respect to the current state of the art, but also contemplates advancements and that adaptations in the future may take into consideration of those advancements, namely in accordance with the then current state of the art. It is intended that the scope of the invention be defined by the Claims as written and equivalents as applicable. Reference to a claim element in the singular is not intended to mean "one and only one" unless explicitly so stated. Moreover, no element, component, nor method or process step in this disclosure is intended to be dedicated to the public regardless of whether the element, component, or step is explicitly recited in the Claims. No claim element herein is to be construed under the provisions of 35 U.S.C. Sec. 112, sixth paragraph, unless the element is expressly recited using the phrase "means for . . . " and no method or process step herein is to be construed under those provisions unless the step, or steps, are expressly recited using the phrase "comprising the step(s) of . . . ."

What is claimed is:

1. A system for measuring properties of a surface under test with surface waves, the system comprising:
   a surface wave network comprising:
      a dielectric substrate;
      a reactive grid comprising a plurality of metallic patches on a first surface of the dielectric substrate;
      a plurality of electronic nodes on the first surface of the dielectric substrate; and
      a ground plane on a second surface of the dielectric substrate opposite the first surface of the dielectric substrate, the ground plane permeable to radio frequency fields of the surface waves; and
   a controller configured for causing a respective one of the electronic nodes to transmit at least one surface wave and configured for collecting data for signals received by at least one other of the plurality of electronic nodes.

2. The system of claim 1 wherein the surface wave network is a laminated structured metamaterial.

3. The system of claim 1 wherein the plurality of metallic patches on a first surface of the dielectric substrate is greater in number than the plurality of electronic nodes on the first surface of the dielectric substrate.

4. The system of claim 1 wherein the metallic patches are printed on the first surface.

5. The system of claim 1 wherein the surface wave network further comprises:
   a thin dielectric sheet laminated to the dielectric substrate; and
   wherein the reactive grid comprising the plurality of metallic patches is on the thin dielectric sheet instead of the dielectric substrate.

6. The system of claim 1 wherein the ground plane comprises a perforated ground plane having an array of holes.

7. The system of claim 1 wherein:
   the controller is configured to send a surface wave signal to a respective one of the electronic nodes; and
   the respective one of the electronic nodes transmits a surface wave in accordance with the surface wave signal.

8. The system of claim 1 wherein:
   the controller is configured to command a respective one of the electronic nodes to transmit a surface wave; and
   the respective one of the electronic nodes is configured to generate a surface wave.

9. The system of claim 1 wherein collecting data for signals received by at least one other of the plurality of electronic nodes comprises collecting amplitude and phase information.

10. The system of claim 1 wherein:
    each electronic node is configured to measure amplitude and phase of signal received, and comprises an analog to digital converter for converting the measured amplitude and phase to digital data.

11. The system of claim 1 wherein:
    the controller comprises a plurality of wires, each wire connected to a respective one of the electronic nodes.

12. The system of claim 1 wherein:
    the controller comprises a wireless network connected to a respective one of the electronic nodes.

13. The system of claim 1 wherein when the surface wave network is located on a surface under test, the RF fields of the surface waves extend through the permeable ground plane into the surface under test.

14. The system of claim 1 wherein the controller further comprises a processor for processing signals received from the electronic nodes, and for creating an image of properties of the surface under test.

15. The system of claim 1 wherein the surface wave network is flexible, and/or stretchable to adapt to complex curvatures.

16. The system of claim 1 wherein the surface wave network further comprises:
    an inflatable bladder; and
    wherein the surface wave network is on the outside of the inflatable bladder, on the inside of the inflatable bladder, or partially on the outside and the inside of the inflatable bladder.

17. The system of claim 16 wherein:
    the electronic nodes are distributed on the inside of the bladder; and
    the permeable ground plane is located on the outside of the bladder.

18. The system of claim 17 wherein:
    the controller comprises a plurality of wires, each wire connected to a respective one of the electronic nodes;
    the bladder comprises a pneumatic cable feedthrough; and
    the plurality of wires pass through the pneumatic cable feedthrough.

19. The system of claim 16 wherein the inflatable bladder is configured to fit within a reentrant cavity of complex curvature.

20. A method of determining a surface characteristic of a surface under test, the method comprising:
    removably locating a surface wave network on the surface under test, wherein the surface wave network comprises:
       a dielectric substrate;
       a reactive grid comprising a plurality of metallic patches on a first surface of the dielectric substrate;
       a plurality of electronic nodes on the first surface of the dielectric substrate; and
       a ground plane on a second surface of the dielectric substrate opposite the first surface of the dielectric substrate, the ground plane permeable to radio frequency fields of the surface waves;
    operating a controller configured for causing a respective one of the electronic nodes to transmit at least one surface wave and configured for collecting data for signals received by at least one other of the plurality of electronic nodes; and
    processing the collected data to determine the surface characteristic of the surface under test.

21. The method of claim 20, wherein processing the collected data further comprises comparing the collected data to baseline collected data from a damage-free surface.

22. The method of claim 20 wherein comparing the collected data to baseline collected data from a damage-free surface further comprises creating an image of the damage to the surface.

23. An apparatus for measuring properties of a surface under test with surface waves comprising:
    a surface wave network comprising:
       a dielectric substrate;
       a reactive grid comprising a plurality of metallic patches on a first surface of the dielectric substrate;
       a plurality of electronic nodes on the first surface of the dielectric substrate; and
       a ground plane on a second surface of the dielectric substrate opposite the first surface of the dielectric substrate, the ground plane permeable to radio frequency fields of the surface waves.

24. The apparatus of claim 23 wherein the surface wave network is a laminated structured metamaterial.

25. The apparatus of claim 23 wherein the surface wave network further comprises:
   a thin dielectric sheet laminated to the dielectric substrate; and
   wherein the reactive grid comprising the plurality of metallic patches is on the thin dielectric sheet instead of the dielectric substrate.

26. The apparatus of claim 23 wherein the ground plane comprises a perforated ground plane having an array of holes.

27. The apparatus of claim 23 wherein:
   each electronic node is configured to measure amplitude and phase of signal received, and comprises an analog to digital converter for converting the measured amplitude and phase to digital data.

28. The apparatus of claim 23 wherein when the surface wave network is located on a surface under test, the RF fields of the surface waves extend through the permeable ground plane into the surface under test.

29. The apparatus of claim 23 wherein the surface wave network is flexible, and/or stretchable to adapt to complex curvatures.

30. The apparatus of claim 23 wherein the surface wave network further comprises:
   an inflatable bladder; and
   wherein the surface wave network is on the outside of the inflatable bladder, on the inside of the inflatable bladder, or partially on the outside and the inside of the inflatable bladder.

31. The apparatus of claim 23 wherein:
   the electronic nodes are distributed on the inside of the bladder; and
   the permeable ground plane is located on the outside of the bladder.

* * * * *